(12) United States Patent
Noordam et al.

(10) Patent No.: US 7,968,705 B2
(45) Date of Patent: Jun. 28, 2011

(54) PRODUCTION OF 5'-RIBONUCLEOTIDES

(75) Inventors: Bertus Noordam, 's-Gravenzande (NL); Jan Gerrit Kortest, Leusden (NL)

(73) Assignee: DSM IP Assets B.V., Te Heerlen (NL)

( * ) Notice: Subject to any disclaimer, the term of this patent is extended or adjusted under 35 U.S.C. 154(b) by 260 days.

(21) Appl. No.: 10/541,194

(22) PCT Filed: Jan. 23, 2004

(86) PCT No.: PCT/EP2004/000658
§ 371 (c)(1),
(2), (4) Date: Jun. 30, 2005

(87) PCT Pub. No.: WO2004/067758
PCT Pub. Date: Aug. 12, 2004

(65) Prior Publication Data
US 2006/0078972 A1    Apr. 13, 2006

(30) Foreign Application Priority Data

Jan. 27, 2003  (EP) ..................................... 03075255

(51) Int. Cl.
*C07H 1/08*   (2006.01)
*A23L 1/229*  (2006.01)
*C07H 19/04*  (2006.01)

(52) U.S. Cl. ......................... 536/127; 536/26.1; 426/537

(58) Field of Classification Search .................. 536/127, 536/26.1; 426/537
See application file for complete search history.

(56) References Cited

U.S. PATENT DOCUMENTS

| 4,303,680 A | * | 12/1981 | Tanekawa et al. | 426/60 |
| 4,374,981 A | * | 2/1983 | Tsuda et al. | 536/27.12 |
| 4,623,723 A | * | 11/1986 | Keller et al. | 536/25.4 |
| 4,649,111 A | | 3/1987 | Keller et al. | |
| 4,741,914 A | * | 5/1988 | Kimizuka et al. | 426/537 |
| 4,810,509 A | * | 3/1989 | Kanegae et al. | 426/60 |
| 5,288,509 A | * | 2/1994 | Potman et al. | 426/60 |

FOREIGN PATENT DOCUMENTS

| DE | 1 420 112 | 12/1968 |
| EP | 0 354 610 | 2/1990 |
| JP | 2002-101846 | 4/2002 |

OTHER PUBLICATIONS

Chae et al. Bioresource Technology, 2001, 76, pp. 253-258.*
Fernandez et al. Acta Biotechnol., 1992, 12(1), p. 49-56.*
Gel Filtration: Principles and Methods, 2002, Amersham Biosciences, edition Al, p.1-34.*
Halasz et al. Use of Yeast Biomass in Food Production, 1991, CRC Press, p. 115-127 and 294-295.*

* cited by examiner

*Primary Examiner* — Shaojia Anna Jiang
*Assistant Examiner* — Jonathan S Lau
(74) *Attorney, Agent, or Firm* — Nixon & Vanderhye P.C.

(57) ABSTRACT

The present invention describes a composition comprising at least 55% w/w (on sodium chloride free dry matter weight) of 5'-ribonucleotides and a process for the production of this composition comprising the steps of: (i) treating microbial cells to release the cell contents comprising RNA; (ii) separating the RNA present in the released cell content from other soluble cell material; and (iii) converting the separated RNA into 5'-ribonucleotides.

16 Claims, No Drawings

PRODUCTION OF 5'-RIBONUCLEOTIDES

This application is the US national phase of international application PCT/EP2004/000658 filed 23 Jan. 2004 which designated the U.S. and claims benefit of EP 03075255.4, dated 27 Jan. 2003, the entire content of which is hereby incorporated by reference.

FIELD OF THE INVENTION

The present invention relates to a composition comprising 5'-ribonucleotides and a process for the production of this composition. The present invention also relates to the use of a composition comprising 5'-ribonucleotides in food or feed.

Autolytic yeast extracts are concentrates of the soluble materials obtained from yeast after disruption of the cells and digestion (lysis) of the polymeric yeast material. The active yeast enzymes released in the medium after cell disruption are responsible for the lysis. Generally these types of yeast extracts do not comprise 5'-ribonucleotides because during the autolytic process the native RNA is decomposed or modified in a form which is not or almost not degradable into 5'-ribonucleotides. These types of yeast extract, which are rich in amino acids, are used in the food industry as basic taste providers. The amino acids present in the yeast extract add a bouillon-like, brothy taste to the food.

Hydrolytic yeast extracts, on the other hand, are concentrates of the soluble materials obtained from yeast after disruption of the cells, digestion (lysis) and addition of proteases and/or peptidases and especially nucleases to the yeast suspension during lysis. The native yeast enzymes are inactivated prior to the lysis. During this process, 5'-ribonucleotides of guanine (5'-guanine mono phosphate; 5'-GMP), uracil (5'-uracil mono phosphate; 5'-UMP), cytosine (5'-cytosine mono phosphate; 5'-CMP) and adenine (5'-adenine mono phosphate; 5'-AMP) are formed. When adenylic deaminase is added to the mixture, 5'-AMP is transformed into 5'-inosine mono phosphate (5'-IMP). The hydrolytic yeast extracts obtained by this method are therefore rich in 5'-ribonucleotides, especially rich in 5'-GMP and 5'-IMP. Often yeast extracts are also rich in mono sodium glutamate (MSG). 5'-IMP, 5'-GMP and MSG are known for their flavour enhancing properties. They are capable of enhancing the savoury and delicious taste in certain types of food. This phenomenon is described as 'mouthfeel' or umami. Yeast extracts rich in 5'-ribonucleotides and, optionally, rich in MSG, are usually added to soups, sauces, marinades and flavour seasonings.

Yeast extracts rich in 5'-ribonucleotides are up to date produced using yeast strains with high RNA content and/or by partial extraction of the cell content. A disadvantage of this type of taste enhancing hydrolytic yeast extracts is that, due to the presence of amino acids, short peptides and other yeast components, they are not very suitable for applications which require cleanliness of taste.

JP 51106791 describes a process for the purification of RNA using ultrafiltration of a yeast extract followed by several additional purification steps. This series of purification steps, which are necessary to obtain a commercially attractive RNA, makes the process complicated and expensive. There is no suggestion in this document of the use of this purified RNA in the production of compositions containing 5'-ribonucleotides, which can be used as taste enhancers in food.

SUMMARY OF THE INVENTION

An object of the present invention is to provide compositions containing a high amount of 5'-ribonucleotides which are clean in taste and can be used in several food or feed applications. Another object of the present invention is to provide a simple and effective process for the production of compositions containing 5'-ribonucleotides with the characteristics mentioned above.

DESCRIPTION OF SPECIFIC EMBODIMENTS OF THE INVENTION

The present invention provides a composition comprising at least 55% w/w (based on the NaCl free, dry matter weight) of 5'-ribonucleotides. The composition preferably comprises at least 65% w/w of 5'-ribonucleotides or more preferably at least 75% w/w of 5'-ribonucleotides. Preferably the composition also comprises glutamate. Typically the composition of the invention comprises at most 98% w/w of 5'-ribonucleotides.

The present invention also provides a process which is very simple and cost-effective and therefore commercially very attractive. Advantageously, the process of the present invention combines the separation of RNA from yeast extracts with the conversion of separated RNA into 5'-ribonucleotides. In this way, it is possible to produce 5'-ribonucleotides having a high purity in a relatively simple and thus commercially very attractive process.

The process of the present invention may be used for the production of the composition of the invention.

Specifically, the present invention provides a process for the production of a composition containing 5'-ribonucleotides which comprises (i) treating microbial cells to release the cell contents comprising RNA;

(ii) separating the RNA present in the released cell contents from other soluble cell material; and (iii) converting the separated RNA into 5'-ribonucleotides.

With the term "5'-ribonucleotides" it is herewith intended to refer to a mixture of 5'-GMP, 5'-CMP, 5'-UMP and further 5'-AMP and/or 5'-IMP, wherein the 5'-IMP in the mixture is obtained by partial or complete conversion of 5'-AMP into 5'-IMP.

The term "5'-ribonucleotides" is herein intended to refer to either the free 5'-ribonucleotides or salts thereof.

The weight percentage of 5'-ribonucleotides in the composition of the invention (% w/w) is based on the weight of the NaCl free dry matter of the composition and is calculated as disodium salt heptahydrate (2Na.7Aq) of 5'-ribonucelotide. NaCl free does not mean that the composition of the invention cannot contain NaCl, but means that NaCl is excluded from the composition for the calculation of % w/w. The latter calculation can be performed by methods known to those skilled in the art. The amount of glutamate in the composition is calculated as glutamic acid percentage (% w/w), i.e. the weight of free glutamic acid per weight of NaCl free dry matter of the composition.

The composition of the invention preferably comprises glutamate wherein the ratio of glutamate to 5'-ribonucleotides is less than 0.1, preferably less than 0.05 or more preferably less than 0.01 and wherein this ratio is more than 0.001. In general the composition comprises from 0.01 to 10%, preferably from 0.05 to 5% or more preferably from 0.1 to 2% w/w of glutamate based on NaCl free dry matter of the composition.

The composition of the invention preferably comprises more 5'-GMP than the sum of 5'-IMP and 5'-AMP. Commercially available yeast extracts all contain less 5'-GMP than the sum of 5'-IMP and 5'-AMP. The 5'-ribonucleotide composition of the present invention, preferably obtained from yeast, contains more 5'-GMP than the sum of 5'-IMP and 5'-AMP. The higher amount of 5'-GMP in respect of the sum of the amounts of 5'-IMP and 5'-AMP in such a composition is advantageous because this results in a stronger flavour enhancing capacity of this composition compared with presently commercially available yeast extracts. This is because 5'-GMP is more functional than 5'-IMP with respect to flavour enhancement, while 5'-AMP does not contribute to flavour enhancement (T. Nagodawithana, "Savoury Flavours", (1995) edited by Esteekay associates, Inc, Wisconsin, USA, page 302).

Any type of microorganism can be used as source of RNA in the process of the invention. Bacterial and fungal microorganisms are preferred, such as those which are suitable for food and feed applications. Preferred microorganisms are those that have the status of being food-grade and thus can be safely applied to food for human consumption. Preferred are microorganisms with a high RNA content.

Examples of microorganisms suitable to be used in the process of the invention include filamentous fungi, such as *Trichoderma* or *Aspergillus*, and yeast. Yeast strains belonging to the genera *Saccharomyces, Kluyveromyces* or *Candida* are preferably used. Yeast strains belonging to the genus *Saccharomyces*, for example to the strain *Saccharomyces cerevisiae* are preferred.

Examples of suitable bacterial microorganisms are lactic acid bacteria, e.g. *Lactobacillus*.

The process of the present invention may start with a fermentation broth of the microorganism in question. Fermentation processes that can be used are known in the art. In some cases the fermentation broth can be concentrated before use in the present process, for example by centrifugation or filtration. For example, cream yeast (Baker's yeast which has been concentrated to 15-27 wt % of dry matter content) may be used.

The fermentation broth is generally obtained from strains with a high RNA content (i.e. typically with a RNA content of 6-15%). In this way a high amount of 5'-ribonucleotides is generated during the hydrolytic process. Although yeast or other microbial strains with high RNA content are preferred, yeast or other microbial strains with a low RNA content can also be used. These yeasts or other microbial strains can be advantageously converted into compositions or yeast extracts having a high 5'-ribonucleotide content using the process of the invention. Furthermore using the process of the present invention, compositions can be obtained having a higher 5'-ribonucleotide content than the content that would be expected on basis of the RNA content of the starting yeast or microorganism and/or the content that is found in presently available yeast extracts.

Prior to treatment of the microbial cells to release the cell content, the microbial cells are preferably treated to inactivate the native enzymes present in the cells. In general, the RNA is degraded or modified in autolytic microbial extracts and separation of this RNA is therefore less attractive.

Inactivation of native enzymes in the fermentation broth is possible with, for example, a heat shock, such as 5 to 10 minutes, suitably at a temperature of 80°-97° C. This treatment should at least inactivate the native enzymes that degrade the RNA of the microorganism (e.g. phosphatase, Rnase, Fdase). Therefore, the RNA of the microorganism will preferably not be degraded or modified after this treatment. RNA degradation may occur at a later stage, for example, by addition of a suitable enzyme.

In the process of the invention microbial cells are treated to release the cell contents comprising RNA. By this treatment, the cell walls are disrupted and/or damaged resulting in release of the cell contents.

In order to release the cell contents from the cells, the cells can be treated chemically, mechanically or enzymatically using methods known to those skilled in the art.

Mechanical treatments include homogenisation techniques. At this purpose, use of high pressure homogenisers is possible. Other homogenisation techniques may involve mixing with particles, e.g. sand and/or glass beads or using of milling apparatus (e.g. a bead mill).

Chemical treatments include the use of salts, alkali and/or one or more surfactants or detergents. Chemical treatments are less preferred because they may lead to partial degradation of RNA especially when alkali is used, with consequent formation of 2'-ribonucleotides and 3'-ribonucleotides.

Preferably, an enzyme is used for this solubilisation or cell wall lysing step because a better control of the process can thereby be achieved. In addition, the use of an enzyme makes this method especially suitable to be used at large scale. Several enzyme preparations can be used comprising cellulases, glucanases, hemicellulases, chitinases, proteases and/or pectinases. For example a protease such as endoprotease can be used. The reaction conditions for the enzyme depend on the enzyme used. In general, the microbial cells are enzymatically treated for from 1 to 24 hours, at a pH of from 4 to 10 and a temperature of from 40 to 70° C.

After the chemical or enzymatical treatment, the chemical(s) or enzyme(s) should preferably be neutralised and/or inactivated under such conditions that the RNA will not be substantially altered and/or degraded.

Inactivation of the enzyme(s) can be done by pH treatment or, preferably, by a heat treatment.

Subsequently the RNA present in the released cell contents is separated from the other soluble microbial cell material.

The soluble RNA can be separated from other soluble materials according to methods known to those skilled in the art, like selective precipitation of the RNA fraction or chromatographic methods. Preferably, separation of the RNA from the other soluble microbial cell material is carried out by ultrafiltration (UF). Ultrafiltration is economically very convenient, is especially suitable for use at large scale and in the production of food grade products. On a laboratory scale, the separation of RNA can be performed in several ways each of which can obtain a very pure sample of small amounts of RNA. These methods are often very labour-intensive and expensive. The present invention provides a process which is especially useful for large scale separation of RNA or 5'-ribonucleotides and which allows the production of RNA or 5'-ribonucleotides on a commercially attractive scale. The present invention provides a process resulting in 5'-ribonucleotides with a good purity and high yield. Large scale means that the starting material in the process of the invention can be a fermentation broth of the microorganism produced in a fermentor of 10 m$^3$ or more.

In cases where UF is used to separate RNA from the other soluble cell material, filters with a molecular weight cut-off of from 10 to 50 kD or preferably from 20 to 50 kD can be used. In general, a larger filter size allows a higher flow through the filter, but might result in larger losses and/or less pure products. The RNA fraction is recovered in the retentate resulting from the ultrafiltration step. It will be clear to those skilled in the art that the amount of 5'-ribonucleotides in the final composition can be influenced by the type of ultrafiltration filter used in the process and by the washing efficiency during the ultrafiltration step.

The separated RNA can be converted into 5'-ribonucleotides, preferably enzymatically.

The enzyme 5'-phosphodiesterase (5'-Fdase) can be used for the conversion of RNA into 5'-ribonucleotides. 5'-phosphodiesterase can be obtained from a microbial or a vegetable source (for example a malt root extract). An example of a commercially available microbial 5'-Fdase is Enzyme RP-1 produced by Amano (Japan). Deaminase, for example adenyl deaminase, can be used to convert 5'-AMP into 5'-IMP. An example of a commercially available deaminase is Deaminase 500 produced by Amano (Japan).

Conversion of RNA into 5'-ribonucleotides by 5'-Fdase and deaminase can be performed in a two-step or in a single step process.

Prior to RNA separation, in a preferred embodiment of the invention, solid material originating from the microbial cells (such as cell walls) is separated from the soluble material (including RNA, proteins, carbohydrates, minerals, lipids and vitamins) present in the released cell content. This can be achieved by any method suitable to perform solid/liquid separation. For example, centrifugation or filtration may be used. When the solid material originating from the microbial cells is not removed before separation of the RNA from the other soluble microbial cell material, the solid material can be removed after conversion of RNA into 5'-ribonucleotides by any solid/liquid separation method.

It will be understood that in the context of the present invention a wording like "separating the RNA present in the released cell content from other soluble cell material" or a wording like "converting the separated RNA into 5'-ribonucleotides" does not necessarily mean that all RNA should be separated or converted, respectively. It will be clear to those skilled in the art that the amount of the RNA which is separated will depend on the type of separation method used and that the amount of RNA which is converted will depend on several factors, for example on the type of enzymes used.

The fraction containing 5'-ribonucleotides obtained after conversion of RNA into 5'-ribonucleotides and optionally after removal of the solid material originating from the microbial cells, is preferably purified from compounds having a higher molecular weight than the 5'-ribonucleotides, preferably by ultrafiltration. The degree of purification will depend on the molecular weight cut-off of the ultrafiltration membrane used.

The fraction containing 5'-ribonucleotides, optionally after purification by ultrafiltration, is generally obtained as a solution which can be further concentrated and/or dried by methods known to those skilled in the art.

The composition comprising 5'-ribonucleotides obtainable by the process of the invention, has a high 5'-ribonucleotide content and is clean in taste. Throughout this specification the wording "clean in taste" means that when the composition of the invention is added to food or feed in proper amounts, any particular taste and/or note typical of the microorganism from which the composition is obtained, or any brothy, bouillon-like taste and/or note coming from the composition is minimal or absent in said food or feed. Preferably any particular taste and/or smell and/or note typical of the microorganism is minimal or absent in the composition of the invention.

For example, the composition may not taste of yeast in cases where *Saccharomyces* was used as the starting material or may not taste sweet in cases where *Candida* was used as the starting material. The composition will not provide bouillon-like or brothy tastes when applied to food products in proper amounts.

According to an embodiment of the invention the 5'-ribonucleotide composition can be added to any conventional yeast extract in any desired ratio. As a consequence, a yeast extract having any desired 5'-ribonucleotide content can be obtained.

The compositions of the inventions originate from a natural source, in particular from a microorganism which is preferably food grade.

The compositions comprising 5'-ribonucleotides according to the invention can be used in any food or feed product, especially to improve and/or enhance the taste and/or aroma and/or mouthfeel thereof. Typical types of food to which said compositions can be added include dairy food, bakery food, vegetables, fruit, meat, confectionery, fat, oils, beverages (for example carbonated beverages or beverages derived from dairy food like milk, from vegetable, fruit, alcoholic drinks, etcetera) or any processed food derived therefrom.

The compositions of the invention find a suitable application in food (or beverages) with reduced or low total fat. In the context of the present invention, the food with a reduced or low total fat is generally obtained from a corresponding full fat food by any processing, formulation or reformulation which leads to the lowering of the total fat comprised therein and/or the replacement of said total fat with a fat replacer. Said processes and said fat replacers are known in the art.

A clear disadvantage of food with reduced or low total fat is that this type of food lacks the richness of flavour of the corresponding full-fat food or beverage product. This disadvantage can be overcome by using the compositions of the invention to improve the fat note in the taste and/or in the aroma and/or in the mouthfeel of food with reduced or low total fat. The latter means that said food with a reduced or low total fat comprising the composition of the invention has a taste and/or aroma and/or mouthfeel that has more resemblance with the taste and/or aroma and/or mouthfeel of the corresponding full-fat food.

The compositions of the invention find another suitable application in food comprising artificial sweeteners. A clear disadvantage related to the use of artificial sweeteners is the presence or development in the food of side or after taste, for example bitterness. The most common artificial sweeteners, which present the above-mentioned problems when used alone or in combination, are: acesulfame-K, alitame, aspartame, cyclamate, neotame, neohesperidine, saccharin, stevioside, sucralose, and thaumatin. This disadvantage can be overcome by using the compositions of the invention to mask the side or aftertaste of an artificial sweetener in food or beverage. The present invention also encompasses compositions comprising an artificial sweetener and the compositions of the invention.

The compositions of the present invention can be used to improve the taste and/or aroma and/or mouthfeel of beverages in more specific terms, in particular to improve the specific vegetable note and/or fruity note and/or alcoholic note in the taste and/or aroma of a beverage. For example they can be used to improve the specific vegetable taste and/or vegetable aroma of vegetable juice, the specific fruit taste and/or fruit aroma of fruit juice or the specific alcoholic taste and/or alcoholic aroma of alcoholic beverage like wine and beer, especially those alcoholic beverages with a low or reduced alcoholic content.

The amount of 5'-ribonucleotide composition to be added to the food or beverage in the above-mentioned applications will depend on the type of food or beverage and on the application. The amount of 5'-ribonucleotide composition can vary for example between 0.0001% w/w and 10% w/w in respect of the food or beverage.

The invention will now be illustrated by some examples which however do not intend to be limiting.

Example 1

40,000 kg of cream yeast (dry solids is 18.2%) was heat treated in a continuous flowthrough heat exchanger for 10 minutes at 95° C. in order to inactivate all yeast enzyme activity. Subsequently, the inactivated yeast was treated batchwise for 6 hours with Pescalase (endo-protease from *Bacillus licheniformis*, DSM N.V., The Netherlands) at pH 8.0 and 62° C. Thereafter, the protease was inactivated by heat treatment for 1 hour at 70° C. (batchwise) and the pH was lowered to 5.3 with hydrochloric acid. The solid material was removed from the reaction mixture by continuous centrifugation. The remaining supernatant was ultrafiltered on a 50 kD ultrafilter to separate the high molecular weight fraction (including RNA) from the low molecular weight material like inorganic components, vitamins, carbohydrates (like trehalose), free amino acids, peptides and small proteins. The high molecular weight fraction (Retentate UF1) was then incubated batchwise for 15 hours at pH 5.3 and 65° C. with the enzyme 5'-phosphodiesterase in order to hydrolyse the RNA into 5'-ribonucleotides. Next, the liberated 5-'AMP was converted into 5'-IMP by the enzyme deaminase during a 2.5 hour incubation at pH 5.1 and 55° C. Finally, the reaction mixture was ultrafiltered again using a 50 kD filter. The filtrate dry solids consisted mainly of 5'-ribonucleotides (filtrate UF2).

Samples were analysed on RNA content and/or on 5'-ribonucleotides content by means of HPLC according to the following methods. RNA in the samples was hydrolysed during an alkaline treatment. GMP (i.e. 2'-GMP and 3'-GMP derived from the hydrolysis of RNA) was quantified by means of HPLC, using 5'-GMP as a standard, using a Whatman Partisil 10-SAX column, a phosphate buffer at pH 3.35 as eluent and UV detection. The weight percentage of RNA content based on sodium chloride free dry matter corresponds to ~4 times the weight percentage of free GMP based on sodium chloride free dry matter.

Filtrate UF2 was also analysed for 5'-GMP, 5'-IMP, 5'-AMP and glutamic acid content. The amount of 5'-GMP, 5'-AMP and 5'-IMP in the samples (expressed as weight percentage of the disodium heptahydrate thereof based on sodium chloride free dry matter) were determined by means of HPLC using a Whatman Partisil 10-SAX column, a phosphate buffer pH 3.35 as eluent and UV detection. Concentrations were calculated on basis of 5'-GMP, 5'-IMP and 5'-AMP standards. The amount of glutamic acid was determined by the L-Glutamic acid Colorimetric-method for the determination of L-glutamic acid in foodstuffs and other materials test kit (Boehringer Mannheim/R-Biopharm, Enzymatic Bio-Analysis/Food Analysis, Catalogue No. 10139092035, Catalogue year 2004, R-BIOPHARM AG, Darmstad, Germany).

Data of the extraction process is presented is Table 1.

TABLE 1 nucleotide extraction process data

| | Amount (kg) | Dry solids (% w/w) | Dry solids (kg) | RNA (%) | 5'GMP* (%) | 5'IMP* (%) | Glutamic acid (%) | 5'AMP*** (%) |
|---|---|---|---|---|---|---|---|---|
| Cream yeast | 40000 | 18.20 | 7280 | 8.2 | | | | |
| Supernatant* | 54100 | 8.77 | 4750 | 10.3 | | | 5.5 | |
| Retentate UF1 | 8120 | 7.80 | 632 | 72.5 | | | 0.4 | |
| Filtrate UF2* | 10160 | 3.98 | 404 | 0.0 | 24.5 | 24.1 | 0.5 | 0 |

*including wash liquid
**% on NaCl free dry solids
***espressed as 2Na.7aq on NaCl free dry solids The amount of 5'-ribonucleotides in the composition is approximately 97% w/w based on sodium chloride free dry matter.

Example 2

A portion of 2100 g of cream yeast (dry solids is 18.2%) was heat treated 10 minutes at 95° C. in order to inactivate all yeast enzyme activity. Subsequently, the inactivated yeast was treated batchwise for 6 hours with Pescalase (endo-protease from *Bacillus licheniformis*, DSM N.V., The Netherlands) at pH 8.0 and 62° C. Thereafter, the protease was inactivated by heat treatment for 1 hour at 70° C. (batchwise) and the pH was lowered to 5.3 with hydrochloric acid. The hydrolysate was ultrafiltered on a 50 kD ultrafilter to separate the high molecular weight fraction (including RNA) and the cell walls from the low molecular weight soluble material like inorganic components, vitamins, carbohydrates (like trehalose), free amino acids, peptides and small proteins. The retentate was incubated batchwise for 15 hours at pH 5.3 and 65° C. with the enzyme 5'-phosphodiesterase in order to hydrolyse the RNA into 5'-ribonucleotides. Next, the liberated 5'-AMP was converted into 5'-IMP by the enzyme deaminase during a 2.5 hour incubation at pH 5.1 and 55° C. Finally, the solids were removed by centrifugation and the pellet fraction was washed with demineralised water and centrifuged again. Both, supernatants (primary supernatant and wash) were combined and the total was ultrafiltered on a 50 kD ultrafilter to separate the low molecular weight material, including the 5'-ribonucleotides, from high molecular weight material. The resulting ultrafiltrate was concentrated and spray dried.

The resulting powder was analysed for its 5'-GMP, 5'-AMP and 5'-IMP concentration. In addition, the glutamic acid and sodium chloride concentration were measured in the final product and the RNA concentration was measured in the cream yeast. Sodium chloride was determined by measuring the chloride ions in the sample with a Jenway chloride meter PCLM 3 (Jenway, Essex, England) and calculating the corresponding amount of sodium chloride. Data of the extraction process is presented is Table 2.

TABLE 2 nucleotide extraction process data (50 kD UF filter)

| | Dry solids (% w/w) | Dry solids (g) | RNA* (%) | NaCl (%) | 5'GMP (%) | 5'IMP (%) | Glutamic acid* (%) | 5'AMP** (%) |
|---|---|---|---|---|---|---|---|---|
| Cream yeast | 18.2 | 383 | 8.2 | 0 | | | | |
| Final powder | 97.4 | | 0.0 | 7.3 | 18.2 | 18.2 | 0.9 | 0.0 |

*% on NaCl free dry solids
**espressed as 2Na.7aq on NaCl free dry solids

The amount of 5'-ribonucleotides in the composition is 73% w/w based on NaCl free dry matter. This amount is lower than the amount in the final product of example 1 (about 97% on NaCl free dry matter). This means that the amount of 5'-ribonucleotides in the composition can be influenced by the type of process.

Example 3

The process was carried out starting from 2100 g of cream yeast (dry solids 18.2%) as described in example 2. However, in this example a 30 kD ultrafilter was applied (50 kD ultrafilter in example 2).

Data of this extraction process is presented in Table 3.

TABLE 3 nucleotide extraction process data (30 kD UF filter)

| | Dry solids (% w/w) | Dry solids (g) | RNA* (%) | NaCl (%) | 5'GMP (%) | 5'IMP (%) | Glutamic acid* (%) | 5'AMP*** (%) |
|---|---|---|---|---|---|---|---|---|
| Cream yeast | 18.50 | 389 | 8.2 | 0 | | | | |
| Final powder | 95.83 | | 0.0 | 5.0 | 19.4 | 16.0 | 0.6 | 3.4 |

*% on NaCl free dry solids
**espressed as 2Na.7aq on NaCl free dry solids

The amount of 5'-ribonucleotides in the composition is about 78% w/w based on NaCl free dry matter. This amount is approximately 5% higher than in the composition produced by means of 50 kD UF filter (example 2). This means that the amount of 5'-ribonucleotides in the composition can be influenced by the type of UF filter.

Example 4

Use of Compositions Containing 5'-Ribonucleotides in Artificially Sweetened Coca Cola® or in Regular Fanta Orange®

The effect of the addition to artificially sweetened Coca Cola® (Cola Cola Light®-Coca Cola Company-Rotterdam) or to regular Fanta Orange® (Coca Cola Company-Rotterdam) of a composition containing 5'-ribonucleotides according to the invention was studied.

The composition contained 17.8% w/w of 5'-GMP, 17.6% w/w of 5'-IMP (i.e. approximately 70% w/w of 5'-ribonucleotides) and 0.7% w/w of glutamic acid on NaCl free dry matter. The sodium chloride content was <1% on dry matter. A dosage of 50 mg of composition per liter of beverage was used.

The taste and/or aroma and/or mouthfeel of the beverages comprising the composition was analysed by a panel of experts in food tasting (experiment 1 and 2) and compared with that of the beverages as such. In the case of Coca Cola Light®, the taste and/or aroma and/or mouthfeel of the beverage comprising the composition was also compared with that of regular Coca Cola® (Coca Cola Company-Rotterdam).

The results are shown in Table 4 (Coca Cola Light®) and in Table 5 (Fanta Orange®), respectively.

TABLE 4

| Experiment | Composition (mg/l) | Observations about taste/aroma |
|---|---|---|
| Coca Cola ® | 0 | Cola, acid, peaky, pungent |
| Coca Cola Light ® | 0 | Cola, less body, chemical after taste |

TABLE 4-continued

| Experiment | Composition (mg/l) | Observations about taste/aroma |
|---|---|---|
| Experiment 1 | 50 | Cola, no chemical after taste, clean, full, more body, more sweet than Coca Cola Light ® more similar to Coca Cola ®, no yeasty notes |

TABLE 5

| Experiment | Composition (mg/l) | Observations about taste/aroma |
|---|---|---|
| Fanta Orange ® | 0 | Orange peel, acid, slightly pungent |
| Experiment 2 | 50 | More full, shift to fruit-flesh, less orange peel, clean orange aroma, more mouthfeel, no yeasty notes |

The results clearly show a positive effect of the ribonucleotide composition on the taste and/or aroma and/or mouthfeel of Coca Cola Light® or Fanta Orange®. In Coca Cola Light® comprising the composition the aftertaste due to the presence of artificial sweeteners (aspartame, sodium cyclamate and acesulphame) in the beverage is masked. In the Fanta Orange® comprising the composition the overall taste, in particular the fruity note therein, is improved.

In addition, no yeasty notes are introduced in the beverage as it would normally be the case when conventional yeast extracts are used. This demonstrates that the compositions according to the invention are clean in taste and are especially suitable for beverage applications where the presence of a yeasty taste/note originating from the yeast extract or composition is not very desirable.

Example 5

Use of Compositions Containing 5'-Ribonucleotides in Processed Cheese

The composition of example 4 was added to a low fat cheese spread (Slimkuipje naturel 15+, comprising 5% w/w of total fat) in a dosage of 50 mg per 100 g of cheese spread. The taste and/or aroma of cheese spread comprising the composition (experiment 1) was analysed by a panel of experts in food tasting and compared with the taste of the cheese spread as such (low fat) and with the taste of the corresponding full fat product (full fat) (Goudkuipje naturel 48+, produced by ERU-Woerden-The Netherlands, comprising 21% w/w of total fat).

The results are shown in table 6.

TABLE 6

| Experiment | Composition (mg/100 g) | Observations about taste/aroma |
| --- | --- | --- |
| Full fat product | 0 | Young Cheese taste, weak aroma, creamy, fatty |
| Low fat product | 0 | Less strong cheese taste, little aroma, not really characteristic of cheese, not creamy, not fatty |
| Experiment 1 | 50 | Stronger cheese aroma than low fat product, more creamy, more fatty, more mouthfeel than low fat product, more similar to full fat product, clean cheese taste, no yeasty notes |

The results clearly show an effect of the compositions of the invention on the taste and/or aroma and/or mouthfeel of processed cheese with low total fat. In particular the taste and/or the aroma and/or the mouthfeel of the low fat spread cheese comprising the composition has more resemblance with the taste and/or the aroma and/or the mouthfeel of the full fat spread cheese. In addition, no yeasty notes originating from the composition are introduced in the food.

The invention claimed is:

1. A process to produce a composition containing 5'-ribonucleotides which comprises:
   (i) treating microbial cells enzymatically to release the cell contents comprising RNA;
   (ii) separating the RNA and the cell walls resulting from step (i) from soluble cell material smaller than 50 kDa;
   (iii) converting the RNA into 5'-ribonucleotides in the presence of the cell walls and in the absence of soluble cell material smaller than 50 kDa; and
   (iv) separating the cell walls from the 5'-ribonucleotides so that a composition containing at least 55% (based on the NaCl-free, dry matter weight) of 5' ribonucleotides is produced.

2. A process according to claim 1, wherein the native enzymes of the microbial cells are inactivated prior to treating the microbial cells to release the cell contents.

3. The process according to claim 1, wherein, in step (iv), the cell walls are removed by centrifugation.

4. The process according to claim 1, wherein the separation of the RNA from the soluble cell material smaller than 50 kDa is carried out by ultrafiltration with a filter and the RNA and the cell walls are recovered in the filter's retentate.

5. The process according to claim 1, wherein, in step (iii), the RNA is enzymatically converted into 5'-ribonucleotides.

6. The process according to claim 1, wherein, after step (iv), the 5'-ribonucleotides are further purified by the removal of compounds having a higher molecular weight than the 5'-ribonucleotides.

7. The process according to claim 6, wherein the removal of compounds having a higher molecular weight than the 5'-ribonucleotides is carried out by ultrafiltration.

8. The process according to claim 1, wherein the composition comprises at least 65% w/w (based on the NaCl free, dry matter weight) of 5'-ribonucleotides.

9. The process according to claim 1, wherein the composition comprises at least 75% w/w (based on the NaCl free, dry matter weight) of 5'-ribonucleotides.

10. The process according to claim 1, wherein the composition comprises 0.01 to 10% w/w (based on the NaCl dry matter weight) of glutamate.

11. The process according to claim 1, wherein the composition comprises more 5'-GMP than the sum of 5'-IMP and 5'-AMP.

12. The process according to claim 1, wherein, in step (i), the cells are treated with a protease.

13. The process according to claim 5, wherein the RNA is enzymatically converted into 5'-ribonucleotides by 5'-phosphodiesterase.

14. The process according to claim 5, wherein the RNA is enzymatically converted into 5'-ribonucleotides by 5'-phosphodiesterase and deaminase.

15. The process according to claim 1, wherein the microbial cells are yeast.

16. The process according to claim 1, wherein the microbial cells are *Saccharomyces cerevisiae*.

* * * * *